United States Patent [19]
Bardenheuer et al.

[11] 4,048,857
[45] Sept. 20, 1977

[54] SAMPLING A STEEL CONVERTER

[76] Inventors: Friedrich Bardenheuer, Immenhofweg 57, 415 Krefeld; Gustav Kolb, 5984 Garbeck, both of Germany

[21] Appl. No.: 751,592

[22] Filed: Dec. 17, 1976

[51] Int. Cl.² ............................................. G01N 1/12
[52] U.S. Cl. ................................ 73/354; 73/425.4 R
[58] Field of Search ............. 73/425.4 R, 354, DIG. 9

[56] References Cited
U.S. PATENT DOCUMENTS

| | | | |
|---|---|---|---|
| 3,457,790 | 7/1969 | Hackett | 73/DIG. 9 |
| 3,756,082 | 9/1973 | Bardenheuer | 73/425.4 R |

Primary Examiner—S. Clement Swisher
Attorney, Agent, or Firm—Ralf H. Siegemund

[57] ABSTRACT

A two-part ceramic probe has a cavity duct pattern of a U, one leg leading to an entrance, the other one being enlarged to define a cavity for a sample proper. A thermo feeler is disposed above that cavity and protected by structure contour of the probe. A second cavity may be disposed above the first one and being filled after the first one.

9 Claims, 6 Drawing Figures

SAMPLING A STEEL CONVERTER

BACKGROUND OF THE INVENTION

The present invention relates to sampling a blowing steel converter by means of a two-part ceramic probe.

The German Pat. No. 2,126,501 discloses a two-part or bi-parted probe being fastened to a tube for sampling molten steel so that its carbon content can be determined. The sample as taken is quite large for ascertaining the liquidus line. Thus, this sample will solidify rather slowly. For this reason, it is a sample in a generalized sense only and not well suited for obtaining quickly a gas analysis as well as a spectrum analysis. A suitable laboratory sample for the latter purpose should be disc-shaped, the disc having a diameter of 32 mm, a thickness of 12 mm and an intake pin of about 6 mm thickness.

Another sampling device could be of the variety in which a disc-shaped sampler is held on a holding tube. A small quartz tube provides for a flow path into the sampling dish. A thermo element is also included in this sampling device. The quartz tube is protected by a metal cap which, however, melts in the liquid steel. Since the cap contains aluminum causing the de-oxidation, the de-oxidizing products flow necessarily into the dish. Also, slag particles can more or less unimpededly enter the sampling disc because the steel has a rather intense flow pattern. The previously mentioned ceramic sampler does not, however, exhibit this drawback due to the downward inclination of the entrance chamber.

DESCRIPTION OF THE INVENTION

It is an object of the present invention to provide a new two-part probe or sampling device by means of which one can take laboratory samples whereby the sample is to be readily accessible following the taking. Moreover, very little nobel metal is to be used in the production of the probe.

In accordance with the preferred embodiment of the present invention, it is suggested to provide a two-part, bi-parted, or two element mold, the parts having preferably mirror image configuration and complementary mold cavities of, overall, U-shaped configuration, wherein one leg leads to a lateral entrance and is sufficiently wide to receive also a piece of aluminum, the other leg is configured to constitute the mold for the sample proper with a narrow inlet duct. A thermo feeler for temperature reading is disposed on the probe above the sample mold; this feeler is embedded in a ceramic body which is placed in a corresponding recess in the mold, beginning in the region of connection to a tube holding the probe and terminating laterally off set therefrom, sufficiently far from the tube, so as not to be affected by gases which usually develop right at the tube.

The sampling mold can be supplemented to provide also a sample for carbon determination. For this, another mold cavity is provided above the first one and being fed through an upwardly leading duct from the duct that contains the aluminum. This way, the mold cavities are filled in the order so that this second sample is, in fact, taken last, just prior to retraction of the probe. The second mold cavity is to be about as wide as it is thick, it may thus be of cubic or spherical configuration. The first and principle mold cavity is preferably disc-shaped, i.e., flat cylindric. The second mold cavity is preferably directly monitored as to temperature by a second thermo feeler.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIGS. 1, 2 and 3 show two parts or mold members 1 and 2 being essentially of mirror symmetrical construction whereby the plane of the drawing of FIG. 1 is the plane of symmetry, denoted by reference numeral 3 in FIGS. 1 and 2. 3 can also be termed the plane of jointure of the two mold members 1 and 2.

Figure 1:
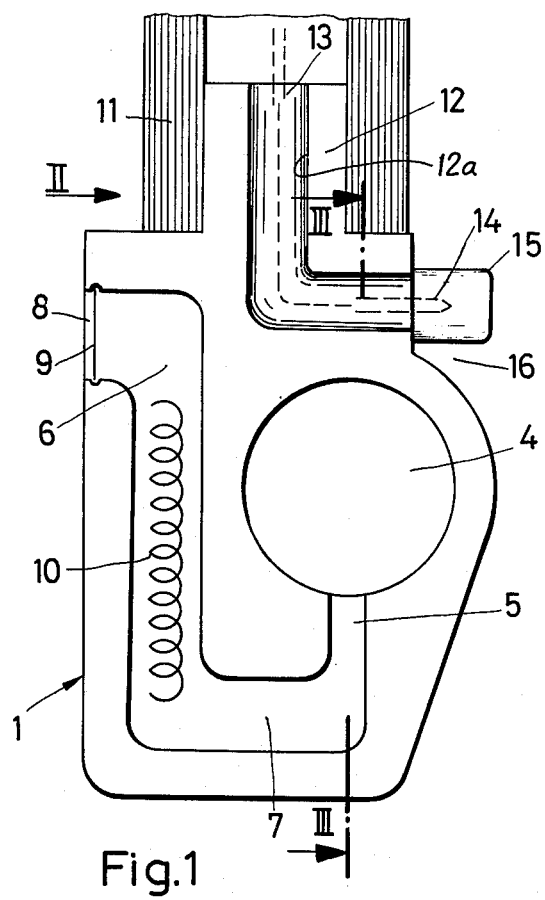
FIG. 1 is a section view through a probe in accordance with the preferred embodiment showing particularly a view into one half of the mold member of the probe.

The two mold parts 1 and 2 are made of ceramic material and are bonded together in plane 3, e.g. they are, for example, bonded through ceramic dross or fired. In either case, they are firmly and tightly interconnected.

Each of the these members 1 and 2 contains one half of the mold cavity portions. These portions are, 4 for the cavity of the sample proper; 5 for the cavity which actually constitutes a duct inlet for cavity 4; 7 a transverse connecting duct that communicates with the inlet cavity duct 5; and 6, an upright feeder duct that extends from an entrance opening 8 to the other end of the transverse duct 7. The opening, entrance or mouth is laterally off set. The mouth 8 has an annular groove which receives a closure disc 9. Cavity duct 6 holds, in addition, an aluminum wire 10 of spiral configuration.

It should be noted that cavity-ducts 6 and 7 have larger diameter than the pin forming cavity 5. All cavities together establish an overall U-shaped cavity. It may readily be assumed that the cavities 4 and 5 have dimensions to produce a disc-shape sample pellet of 32 mm (about 1 9/32 inches) diameter, 12 mm (about ½ inch) thickness with a pin (inlet 5) of 6 mm (or about ¼ inch) diameter.

The mold members each have, in addition, one half of a connecting pin 12 by means of which the members are stuck into a thick-walled cardboard tube 11. Alternatively or additionally, the mold members could be provided with socket halves into which tube 11 is stuck. In either case, the tube 11 must be bonded to the mold halves.

It should be noted that tube 11 is not provided for holding the mold members together. Rather, the ceramic members 1 and 2 should be fired for bonding or a suitable ceramic bonding agent is provided to fasten members 1 and 2 to each other as stated above.

The interfaces of the two members 1 and 2, or one thereof, may additionally have venting ducts that lead from cavity 4 to the interior tube 11. Additionally, the mold members each have a complementary duct portion 12a of angular configuration so that the resulting duct communicates with the interior of tube 11 but terminates laterally. That L-shaped duct is filled with a ceramic body 13 of like configuration in which are embedded the wires of a thermo feeler established particularly by a thermocouple 14 that projects from the short leg of the L. The thermocouple is initially covered by a cap 15 for projecting the thermo feeler 14.

The thermo feeler is placed sufficiently far from the end of carboard tube 11 so that reaction gases as formed thereat quite vigorously will not interfer with the temperature measurement. Another aspect to be considered is that this thermo feeler holer 13 is quite short and very little expensive platinum wire is needed.

The temperature measuring point as established in this fashion is located about opposite to the mold entrance 8. Moreover, cap 15 and its content are protected by a projection 16 as it results from the pellet contour of the principle mold cavity 4. This way, the thermo feeler is protected additionally as the probe is lowered into the steel bath. Generally speaking, the lateral bulging onto contour of the member 1 and 2 places itself between the impact sensitive temperature measuring device (14 and 15 before the latter melts) and the steel into which the probe is pushed.

Upon inserting the device as shown into a blowing converter, disc 9 and cap 15 melt rather rapidly. Thus, as steel begins to pour into duct 6, its temperature is already being measured. As the dis-quieted steel pours into duct 6, aluminum coil 10 oxidizes immediately, but the flow of steel does not carry coil 10 into entrance duct 5 for mold cavity 4 due to the narrow cross-section of the latter duct. Coil 10 remains as scale or slag in duct 6, 7. Thus, the steel as actually flowing into mold cavity 4 is indeed representative of the state of the steel in the converter in the instant of sampling.

Figure 3:
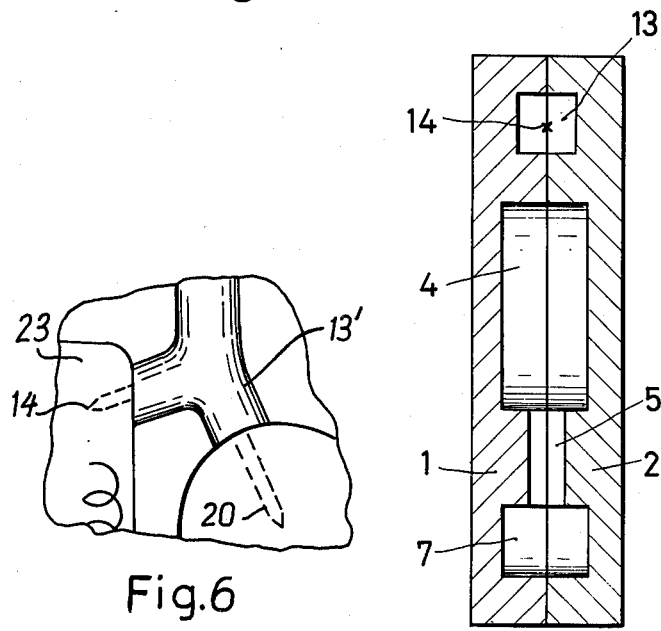
FIG. 3 is a section view taken along lines III—III in FIG. 1.
Figures 4, 5:
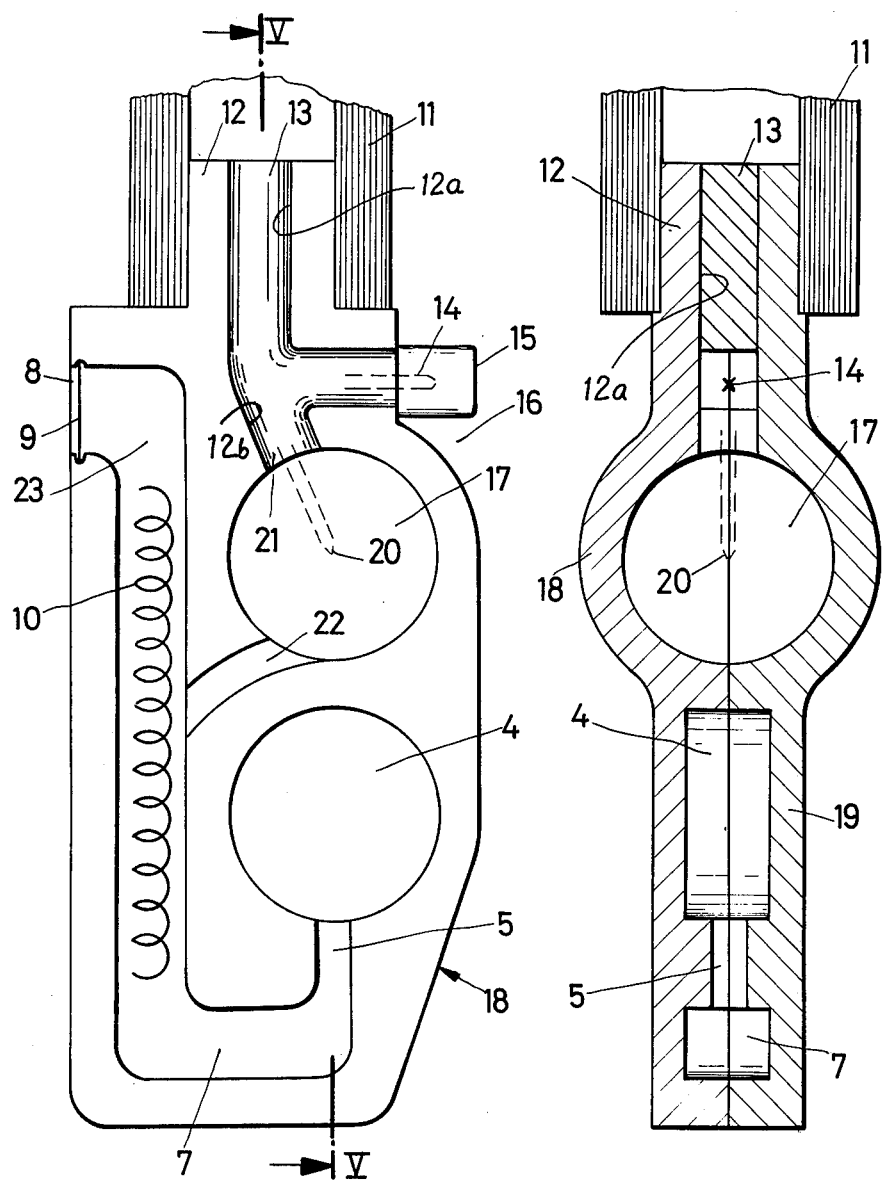
FIG. 4 is a view analogous to FIG. 1 but through a more elaborate sampling device.
FIG. 5 is a section view taken along line V—V of FIG. 4.

Turning now to FIGS. 4 and 5, the sampling device as shown provides for sampling and temperature measurement as outlined above; in addition, special provisions are made for the determination of the carbon content of the melt. The two mold parts are denoted here by reference numerals 18 and 19, but the cavities which are the same as in FIGS. 1, 2, 3 have the same reference numerals. Thus, 4 is the cavity for the sampler proper with inlet ducts 5, 7, and the entrance 8 is closed by disc 9. Also, parts or portions 12, 13, 14, and 15 are the same, and parts 18 and 19 are bonded together, as are parts 1 and 2. The probe exhibits, however, the following differences.

Figure 2:
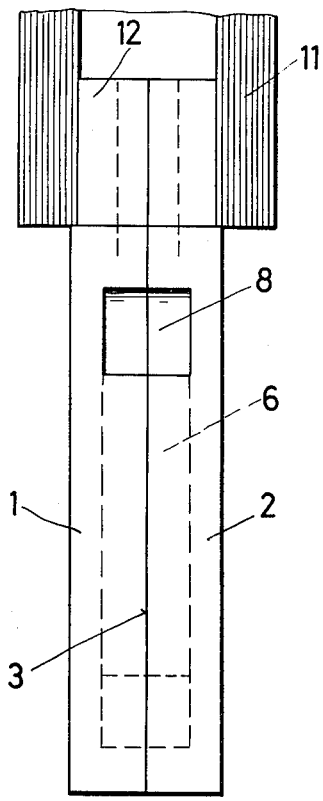
FIG. 2 is a front view taken along the line II of FIG. 1 and showing also the section plane 3 for the view of FIG. 1.

First of all, upright feeder duct 23 is longer than the corresponding duct 6 in FIGS. 1, 2, 3. A second mold cavity 17 is provided through complementary cavities in members 18 and 19. Each cavity half is a semisphere for obtaining a spherical sample, i.e., a sample that is as wide as it is thick, at least approximately so. In view of this condition, the cavity could be a cube or an appproximation thereof. The members 18, 19 have, of course, a pronounced bulge in the region of this rather thick cavity 17.

A duct 12b extends from duct 12a and contains also a ceramic extension 2 of body 13, in which is embedded the connection to a second thermocouple 20. Of course, the electrical connections to the thermo feeders 14 and 20 must be appropriately electrically isolated as to their respective signal paths. This body 21 carrying thermocoupler 20 closes the cavity 17 from above.

A branch duct 22 provides for access to cavity 17, leading from the upright feeder duct 23 at an oblique, upward angle to the bottom of cavity 17. The various ducts and cavities communicate with each other in such a manner that steel does not flow into cavity 17 until cavity 4 is filled. Steel descending in duct 23 will, in fact, descend all the way down and not flow up in duct 22 until the static liquid level in the entire system has reached the level of duct 22. The convex curvature of duct 22 avoids formation of stagnating steel during the filling phase of cavity 4.

It can readily be seen that the sampling devices in accordance with the present invention are of rather practical configuration. The sample proper has the desired configuration as to its use for spectrum and gas analyses. On the other hand, the construction as a whole is readily supplementable as to the taking of a second sample for carbon analysis. Slag cannot enter the mold cavities, and the thermo feelers are readily protected but the connections of the thermo feeler are comparatively short. The thermo feelers are independently made and laid in when the mold is closed. The mold can be destroyed following retraction to release the content.

Figure 6:
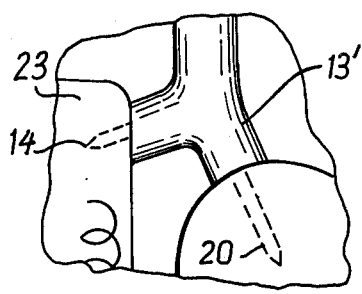
FIG. 6 shows in detail a modification of the sampling device of FIGS. 4 and 5.

The apparatus as described can be modified by placing the thermocouple 14 into or near the entrance 8, i.e., in the upper portion of duct 6 or 23. FIG. 6 shows that modification for the probe as shown in FIGS. 4 and 5. The bend-off or off set portion of the feeder duct is particularly suitable because upon adaptation of the contour one can readily avoid any constriction of the liquid passage on account of the thermocoupler. This modification has the advantage that cap 15 can be eliminated. Also, the ceramic part containing thermocoupler 14 would be better protected in and by the duct 23 or 6.

The invention is not limited to the embodiments described above but all changes and modifications thereof not constituting departures from the spirit and scope of the invention are intended to be included.

We claim:

1. A probe for sampling steel from a blowing steel converter or the like, to be fastened to a tube, comprising:
   a pair of elements with complementary mold cavity halves each to define mold cavities when assembled, the mold cavities including (a) a first, inner portion for the sampled steel; (b) a downwardly oriented inlet duct communicating with the first portion; (c) a traverse duct extending from said inlet duct; and (d) an upright feeler duct leading from an entrance above a level for the inner portion to the transverse duct; and
   a thermo feeler disposed above the said inner portion for measuring the steel temperature when the probe is inserted in molten steel.

2. A probe as in claim 1, wherein the inlet duct is narrower than the transverse and the feeler ducts.

3. A probe as in claim 1, wherein a duct is provided in the upper portion of the probe for containing the thermo feeler.

4. A probe as in claim 3, the latter duct having a downwardly directed portion for communicating with said tube, and a lateral portion for the thermo feeler, the thermo feeler being protected by at least a portion of the probe.

5. A probe as in claim 1, and including a second mold cavity, fluid conductively connected to the upright duct.

6. A probe as in claim 5, wherein said second cavity and its connections have relative position to be filled after the first mentioned mold cavity.

7. A probe as in claim 1, each element having a complementary connection extension by means of which the probe can be connected to a tube, the elements each having a complementary L-shaped duct, the long arm thereof extending into the connection, and an insert placed in the L-shaped duct holding a thermo feeler having an end that is exposed to steel when the probe is inserted into a steel bath.

8. A probe as in claim 7, said thermo feeder end extending behind a bulging portion of the elements and being covered by a cap.

9. A probe as in claim 7, said thermo feeder extending into the upright feeler duct.

* * * * *